(12) United States Patent
Senoo et al.

(10) Patent No.: US 9,724,451 B2
(45) Date of Patent: Aug. 8, 2017

(54) SILICONE RUBBER-BASED CURABLE COMPOSITION, METHOD FOR PRODUCING SILICONE RUBBER, SILICONE RUBBER, MOLDED ARTICLE, AND TUBE FOR MEDICAL USE

(75) Inventors: Kazunobu Senoo, Tokyo (JP); Jun Okada, Tokyo (JP); Motoyoshi Tsujimoto, Tokyo (JP)

(73) Assignee: SUMITOMO BAKELITE CO., LTD., Tokyo (JP)

(*) Notice: Subject to any disclaimer, the term of this patent is extended or adjusted under 35 U.S.C. 154(b) by 107 days.

(21) Appl. No.: 14/007,622

(22) PCT Filed: Mar. 29, 2012

(86) PCT No.: PCT/JP2012/058341
§ 371 (c)(1),
(2), (4) Date: Sep. 25, 2013

(87) PCT Pub. No.: WO2012/133639
PCT Pub. Date: Oct. 4, 2012

(65) Prior Publication Data
US 2014/0018464 A1    Jan. 16, 2014

(30) Foreign Application Priority Data

Mar. 31, 2011  (JP) ................ 2011-080361
Mar. 31, 2011  (JP) ................ 2011-080362

(51) Int. Cl.
| C08L 83/04 | (2006.01) |
|---|---|
| C08L 83/00 | (2006.01) |
| A61L 29/04 | (2006.01) |
| C08G 77/12 | (2006.01) |
| C08G 77/20 | (2006.01) |

(52) U.S. Cl.
CPC .......... *A61L 29/049* (2013.01); *A61L 29/042* (2013.01); *C08L 83/04* (2013.01); *C08G 77/12* (2013.01); *C08G 77/20* (2013.01)

(58) Field of Classification Search
None
See application file for complete search history.

(56) References Cited

U.S. PATENT DOCUMENTS

| 2,371,068 | A | * | 3/1945 | Rochow | C08G 77/08 528/14 |
|---|---|---|---|---|---|
| 2,375,993 | A | * | 5/1945 | Hulbert | F41A 9/00 206/3 |
| 2,431,878 | A | * | 12/1947 | McGregor | C08G 77/08 128/DIG. 21 |
| 3,020,260 | A | * | 2/1962 | Nelson | A61F 2/12 174/521 |
| 3,344,111 | A | * | 9/1967 | Chalk | C08F 4/06 525/478 |
| 3,445,420 | A | * | 5/1969 | Kookootsedes | C08L 83/04 128/DIG. 21 |
| 3,671,480 | A | | 6/1972 | Wada et al. | |
| 3,884,866 | A | | 5/1975 | Jaram et al. | |
| 4,010,136 | A | * | 3/1977 | Blizzard | C08L 83/04 524/506 |
| 4,061,609 | A | * | 12/1977 | Bobear | C08L 83/04 523/212 |
| 4,539,357 | A | | 9/1985 | Bobear | |
| 5,364,921 | A | * | 11/1994 | Gray | C08L 83/04 156/307.1 |
| 2004/0082736 | A1 | * | 4/2004 | Sakamoto | C08G 77/44 525/477 |
| 2013/0065999 | A1 | * | 3/2013 | Takanashi | H01L 23/295 524/268 |
| 2015/0045487 | A1 | * | 2/2015 | Takanashi | H01L 23/295 524/268 |

FOREIGN PATENT DOCUMENTS

| JP | 03-039360 A | 2/1991 |
|---|---|---|
| JP | 04-359057 A | 12/1992 |
| JP | 06-041435 A | 2/1994 |
| JP | 07-133433 A | 5/1995 |
| JP | 07-228782 A | 8/1995 |
| JP | 07-258551 A | 10/1995 |
| JP | 07-331079 A | 12/1995 |
| JP | 08-269339 A | 10/1996 |
| JP | 2004323764 A | * 11/2004 |
| JP | 2010-013495 A | 1/2010 |
| JP | 2010013495 A | * 1/2010 |

OTHER PUBLICATIONS

Silicone Fluid Permance and Test Results, Shin-Etsu, 2005.*
International Search Report dated Jul. 10, 2012, issued in corresponding application No. PCT/JP2012/058341.

* cited by examiner

*Primary Examiner* — Peter A Salamon
(74) *Attorney, Agent, or Firm* — Westerman, Hattori, Daniels & Adrian, LLP

(57) ABSTRACT

The present invention provides a silicone rubber-based curable composition with which a silicone rubber having excellent tensile strength and tear strength is obtained, a method for producing a silicone rubber using the silicone rubber-based curable composition, a silicone rubber, a molded article using the silicone rubber, and a tube for medical use formed from the molded article. The silicone rubber-based curable composition of the present invention is characterized in that it includes a vinyl group-containing organopolysiloxane (A), an organohydrogen polysiloxane (B), silica particles (C), a silane coupling agent (D), and platinum or a platinum compound (E).

15 Claims, No Drawings

SILICONE RUBBER-BASED CURABLE COMPOSITION, METHOD FOR PRODUCING SILICONE RUBBER, SILICONE RUBBER, MOLDED ARTICLE, AND TUBE FOR MEDICAL USE

TECHNICAL FIELD

The present invention relates to a silicone rubber-based curable composition, a method for producing a silicone rubber, a silicone rubber, a molded article, and a tube for medical use.

Priority is claimed on Japanese Patent Application No. 2011-80361 filed on Mar. 31, 2011, and Japanese Patent Application No. 2011-80362 filed on Mar. 31, 2011, the contents of which are hereby incorporated by reference in their entirety.

BACKGROUND ART

A silicone rubber is excellent in heat resistance, flame retardancy, chemical stability, weather resistance, radiation resistance, electrical characteristics, and the like, and is therefore used in various applications in a wide range of fields.

In particular, since the silicone rubber is physiologically inactive and has little response to body tissues when it is brought into contact with living bodies, it is therefore used as a material for medical instruments such as various catheters for medical uses.

A catheter for medical use is a tube which is inserted into a body cavity such as an abdominal cavity and a chest cavity, a tube cavity part such as the digestive tract and the urinary tract, blood vessels, or the like, and is therefore used for fluid drainage or for injecting and dripping of chemical liquids, nutritional agents, contrast agents, or the like. The catheter for medical use is required to have, in addition to biocompatibility, scratch resistance (tear resistance), kink resistance (tensile strength and compression permanent strain), transparency, flexibility (tensile elongation), and the like. Examples of the specific applications of the catheter for medical use include a drainage tube of an aspirator for removing drainage such as blood and pus, and a tube for nutrition intake after surgery such as percutaneous endoscopic gastrostomy (PEG). Further, in order to produce ultrafine tubular silicone rubber for a catheter, a silicone rubber composition which is a material of the silicone rubber is required to have extrusion moldability.

As the material of the catheter for medical use, in addition to a silicone rubber, soft polyvinyl chloride or the like is generally used. As compared with polyvinyl chloride, the silicone rubber is excellent in biocompatibility and flexibility, but is required to have a decreased compression permanent strain, which is indicative of a restoring force, and is also required to have a surface having improved strength such as tear strength and tensile strength, in particular, tear strength. If the tear strength is not sufficient, the catheter may be torn by a scratch by a knife, a needle, or the like during a treatment; and if the tensile strength and the compression permanent strain are not sufficient, the catheter bends and yields, and thus becomes obstructed (kinked). As a result, the flow of a fluid which needs to be discharged or a chemical liquid which needs to be injected in a catheter is interrupted.

Therefore, in order to improve the tear strength, the compression permanent strain, and the tensile strength of a silicone rubber (for example, PTLs 1 to 7), various methods have been proposed. Examples of the specific method for providing the silicone rubber with high tear resistance include the addition of an inorganic filler or the like and the increase in a crosslink density (distribution of an area having a high crosslink density and an area having a low crosslink density in a silicone fine particle system). The reason therefor is thought to be that the improvement of the tear resistance by increasing the crosslink density makes the area having a high crosslink density act as a resistance to tearing stress.

More specifically, in PTL 1, a curable silicone rubber composition is disclosed having an organopolysiloxane (raw rubber (A)) having a high viscosity and a low content of vinyl groups, which is blended with an organopolysiloxane (silicone oil (B)) having a low viscosity and a high content of vinyl groups, a vinyl group-containing organopolysiloxane copolymer (vinyl group-containing silicone resin (C)), an organohydrogen siloxane (crosslinking agent (D)), platinum or a platinum compound (curing catalyst (E)), and fine powder silica (filler (F)).

However, even though an organopolysiloxane having a high content of vinyl groups is used and blended in combination with an organopolysiloxane having a different content of vinyl groups as in PTL 1, it is possible to increase the tensile strength by increasing the cross-linking points, but there remains a problem in that a sufficient tear strength is not obtained and further, the compression permanent strain is not decreased.

CITATION LIST

Patent Literature

PTL 1: Japanese Unexamined Patent Application, First Publication No. H07-331079
PTL 2: Japanese Unexamined Patent Application, First Publication No. H07-228782
PTL 3: Japanese Unexamined Patent Application, First Publication No. H07-258551
PTL 4: U.S. Pat. No. 3,884,866
PTL 5: U.S. Pat. No. 4,539,357
PTL 6: U.S. Pat. No. 4,061,609
PTL 7: U.S. Pat. No. 3,671,480

It is an object of the present invention to provide a silicone rubber-based curable composition with which a silicone rubber having excellent tensile strength and tear strength as well as a low compression permanent strain is obtained, a method for producing a silicone rubber using the silicone rubber-based curable composition, a silicone rubber, a molded article using the silicone rubber, and a tube for medical use formed from the molded article.

Solution to Problem

This object is accomplished by the present invention as described in (1) to (29) below.
(1) A silicone rubber-based curable composition including a vinyl group-containing organopolysiloxane (A), an organohydrogen polysiloxane (B), silica particles (C), a silane coupling agent (D), and platinum or a platinum compound (E).
(2) The silicone rubber-based curable composition as described in (1), which is formed by obtaining a kneaded product containing the vinyl group-containing organopolysiloxane (A), the silica particles (C), and the silane coupling agent (D), and then kneading the kneaded product with the organohydrogen polysiloxane (B) and the platinum or platinum compound (E).

(3) The silicone rubber-based curable composition as described in (2), in which the kneaded product is obtained by kneading the vinyl group-containing organopolysiloxane (A) with the silane coupling agent (D) in advance, and then kneading the silica particles (C) therewith.

(4) The silicone rubber-based curable composition as described in (2) or (3), which is obtained by kneading the organohydrogen polysiloxane (B) with the kneaded product, kneading the platinum or platinum compound (E) with the kneaded product, and then kneading them with each other.

(5) The silicone rubber-based curable composition as described in any one of (1) to (4), further including water (F).

(6) The silicone rubber-based curable composition as described in any one of (1) to (5), in which the vinyl group-containing organopolysiloxane (A) is a vinyl group-containing linear organopolysiloxane (A1).

(7) The silicone rubber-based curable composition as described in (6), in which the vinyl group-containing linear organopolysiloxane (A1) is represented by the following formula (1):

[Chem. 1]

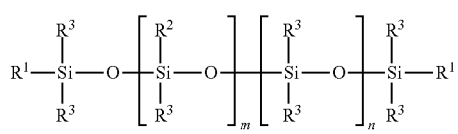

(1)

(in the formula (1), m is an integer of 1 to 1000, n is an integer of 3000 to 10000, $R^1$ is a substituted or unsubstituted alkyl group, alkenyl group, or aryl group having 1 to 10 carbon atoms, or a hydrocarbon group formed by the combination of these groups, $R^2$ is a substituted or unsubstituted alkyl group, alkenyl group, or aryl group having 1 to 10 carbon atoms, or a hydrocarbon group formed by the combination of these groups, and $R^3$ is a substituted or unsubstituted alkyl group or aryl group having 1 to 8 carbon atoms, or a hydrocarbon group formed by the combination of these groups).

(8) The silicone rubber-based curable composition as described in (6) or (7), in which the vinyl group-containing organopolysiloxane (A1) contains a first vinyl group-containing linear organopolysiloxane (A1-1) and a second vinyl group-containing linear organopolysiloxane (A1-2), having different contents of the vinyl groups.

(9) The silicone rubber-based curable composition as described in (8), in which the content of the vinyl groups of the first vinyl group-containing linear organopolysiloxane (A1-1) is from 0.05% by mole to 0.2% by mole, and the content of the vinyl groups of the second vinyl group-containing linear organopolysiloxane (A1-2) is from 0.5% by mole to 12% by mole.

(10) The silicone rubber-based curable composition as described in any one of (1) to (9), in which the organohydrogen polysiloxane (B) is a linear organohydrogen polysiloxane (B1).

(11) The silicone rubber-based curable composition as described in (10), in which the linear organohydrogen polysiloxane (B1) is represented by the following formula (2):

[Chem. 2]

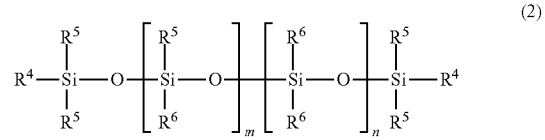

(2)

(in the formula (2), in is an integer of 0 to 300 and n is an integer of (300-m). $R^4$ is a substituted or unsubstituted alkyl group, alkenyl group, or aryl group having 1 to 10 carbon atoms, a hydrocarbon group formed by the combination of these groups, or a hydride group. $R^5$ is a substituted or unsubstituted alkyl group, alkenyl group, or aryl group having 1 to 10 carbon atoms, a hydrocarbon group formed by the combination of these groups, or a hydride group. However, at least two or more out of plural $R^4$s and $R^5$s are hydride groups. $R^6$ is a substituted or unsubstituted alkyl group or aryl group having 1 to 8 carbon atoms, or a hydrocarbon group formed by the combination of these groups).

(12) The silicone rubber-based curable composition as described in any one of (1) to (11), in which the silane coupling agent (D) has a hydrolyzable group that undergoes a dehydrative condensation reaction with a hydroxyl group provided in the silica particles (C) after hydrolysis.

(13) The silicone rubber-based curable composition as described in (12), in which the silane coupling agent (D) has a hydrophobic group.

(14) The silicone rubber-based curable composition as described in (12) or (13), in which the silane coupling agent (D) has a vinyl group.

(15) The silicone rubber-based curable composition as described in (1), further including both of a linear organohydrogen polysiloxane having a linear structure (B1) and a branched organohydrogen polysiloxane having a branched structure (B2) as the organohydrogen polysiloxane (B).

(16) The silicone rubber-based curable composition as described in (15), which is formed by obtaining a kneaded product containing the vinyl group-containing organopolysiloxane (A), the silica particles (C), and the silane coupling agent (D), and then kneading the kneaded product with the organohydrogen polysiloxane (B) and the platinum or platinum compound (E).

(17) The silicone rubber-based curable composition as described in (16), in which the kneaded product is obtained by kneading the vinyl group-containing organopolysiloxane (A) with the silane coupling agent (D) in advance, and then kneading the silica particles (C) therewith.

(18) The silicone rubber-based curable composition as described in (16) or (17), which is obtained by kneading the organohydrogen polysiloxane (B) with the kneaded product, kneading the platinum or platinum compound (E) with the kneaded product, and then kneading them with each other.

(19) The silicone rubber-based curable composition as described in any one of (15) to (18), further including water (F).

(20) The silicone rubber-based curable composition as described in any one of (15) to (19), in which the vinyl group-containing organopolysiloxane (A) is a vinyl group-containing linear organopolysiloxane (A1).

(21) The silicone rubber-based curable composition as described in (20), in which the vinyl group-containing linear organopolysiloxane (A1) is represented by the following formula (1):

[Chem. 3]

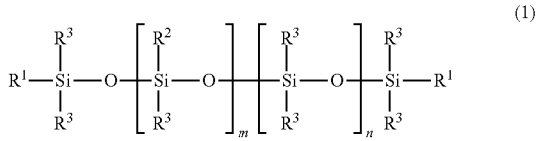

(1)

(in the formula (1), m is an integer of 1 to 1000, n is an integer of 3000 to 10000, $R^1$ is a substituted or unsubstituted alkyl group, alkenyl group, or aryl group having 1 to 10 carbon atoms, or a hydrocarbon group formed by the combination of these groups, $R^2$ is a substituted or unsubstituted alkyl group, alkenyl group, or aryl group having 1 to 10 carbon atoms, or a hydrocarbon group formed by the combination of these groups, and $R^3$ is a substituted or unsubstituted alkyl group or aryl group having 1 to 8 carbon atoms, or a hydrocarbon group formed by the combination of these groups).

(22) The silicone rubber-based curable composition as described in any one of (15) to (21), in which the linear organohydrogen polysiloxane (B1) is represented by the following formula (2):

[Chem. 4]

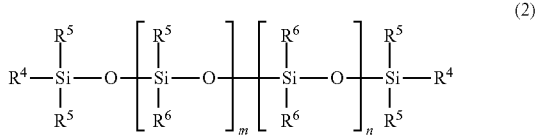

(2)

(in the formula (2), m is an integer of 0 to 300 and n is an integer of (300-m). $R^4$ is a substituted or unsubstituted alkyl group, alkenyl group, or aryl group having 1 to 10 carbon atoms, a hydrocarbon group formed by the combination of these groups, or a hydride group. $R^5$ is a substituted or unsubstituted alkyl group, alkenyl group, or aryl group having 1 to 10 carbon atoms, a hydrocarbon group formed by the combination of these groups, or a hydride group. However, at least two or more out of plural $R^4$s and $R^5$s are hydride groups. $R^6$ is a substituted or unsubstituted alkyl group or aryl group having 1 to 8 carbon atoms, or a hydrocarbon group formed by the combination of these groups).

(23) The silicone rubber-based curable composition as described in any one of (15) to (22), in which the branched organohydrogen polysiloxane (B2) is represented by the following average composition formula (c):

average composition formula (c): 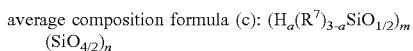

(in the formula (c), $R^7$ is a monovalent organic group, a is an integer in the range of 1 to 3, m is the number of $H_a(R^7)_{3-a}SiO_{1/2}$ units, and n is the number of $SiO_{4/2}$ units).

(24) The silicone rubber-based curable composition as described in any one of (15) to (23), in which the silane coupling agent (D) has a hydroxyl group provided in the silica particles (C), and a hydrolyzable group that undergoes a dehydrative condensation reaction after hydrolysis.

(25) The silicone rubber-based curable composition as described in (24), in which the silane coupling agent (D) has a hydrophobic group.

(26) The silicone rubber-based curable composition as described in (24) or (25), in which the silane coupling agent (D) has a vinyl group.

(27) A method for producing a silicone rubber, including:
a step of obtaining a kneaded product containing a vinyl group-containing organopolysiloxane (A), silica particles (C), and a silane coupling agent (D);
a step of obtaining a silicone rubber-based curable composition by kneading the kneaded product with an organohydrogen polysiloxane (B) and platinum or a platinum compound (E); and
a step of forming a silicone rubber by curing the silicone rubber-based curable composition.

(28) The method for producing a silicone rubber as described in (27), in which both of a linear organohydrogen polysiloxane (B1) and a branched organohydrogen polysiloxane (B2) are contained as the organohydrogen polysiloxane (B).

(29) A silicone rubber formed by curing the silicone rubber-based curable composition as described in any one of (1) to (26).

(30) A molded article formed by using the silicone rubber as described in (29).

(31) A tube for medical use formed from the molded article as described in (30).

ADVANTAGEOUS EFFECTS OF INVENTION

A silicone rubber obtained by curing the silicone rubber-based curable composition of the present invention, that is, a silicone rubber produced by the method for producing a silicone rubber of the present invention has excellent tensile strength and tear strength as well as a low compression permanent strain. Thus, a molded article formed using the obtained silicone rubber and a tube for medical use formed from the molded article have high mechanical strength such as tensile strength and tear strength as well as a low compression permanent strain.

Furthermore, by using a silane coupling agent having a vinyl group as the silane coupling agent included in the silicone rubber-based curable composition, a high hardness, a high modulus, and a high restorability (high rubber elasticity) of the silicone rubber thus formed are promoted.

Here, as a material of the catheter for medical use, the silicone rubber is required to have a certain degree of hardness. For example, a catheter formed from a material having a low hardness easily causes problems, for example, generation of deformation by insertion resistance upon insertion into a target site (for example, thoracic cavity) (there is no so-called waist), low kink resistance, and generation of obstructions. To the contrary, by promoting the silicone rubber having a high hardness, a high modulus, and a high restorability (high rubber elasticity), a catheter formed from the silicone rubber solves the above-described problems.

DESCRIPTION OF EMBODIMENTS

Hereinafter, in one embodiment of the present invention, the silicone rubber-based curable composition, the molded article, and the tube for medical use will be described in detail, based on suitable embodiments.

<Silicone Rubber-Based Curable Composition>

First, the silicone rubber-based curable composition of the present invention will be described.

The silicone rubber-based curable composition of the present invention includes a vinyl group-containing organopolysiloxane (A), an organohydrogen polysiloxane (B), silica particles (C), a silane coupling agent (D), and platinum or a platinum compound (E).

Hereinafter, the respective components constituting the silicone rubber-based curable composition of the present invention will be described sequentially.

<<Vinyl Group-Containing Organopolysiloxane (A)>>

The vinyl group-containing organopolysiloxane (A) is a polymerization product that is a main component of the silicone rubber-based curable composition of the present invention.

As the vinyl group-containing organopolysiloxane (A), a vinyl group-containing linear organopolysiloxane having a linear structure (A1) is used.

The vinyl group-containing linear organopolysiloxane (A1) has a linear structure, and contains vinyl groups, and these vinyl groups become crosslinking points during the curing.

The content of the vinyl groups of the vinyl group-containing linear organopolysiloxane (A1) is not particularly limited, but is preferably from 0.01% by mole to 15% by mole, and more preferably from 0.05% by mole to 12% by mole. As a result, the amount of the vinyl groups in the vinyl group-containing linear organopolysiloxane (A1) is optimized, and carrying out the formation of a network with the respective components which will be described later is ensured.

Furthermore, in the present specification, the content of the vinyl groups refers to an amount in % by mole of the vinyl group-containing siloxane units when the amount of all the units forming the vinyl group-containing linear organopolysiloxane (A1) is taken as 100% by mole. However, it is considered that one vinyl group corresponds to one vinyl group-containing siloxane unit.

In addition, the polymerization degree of the vinyl group-containing linear organopolysiloxane (A1) is not particularly limited, but is preferably in the range of about 3000 to 10000, and more preferably in the range of about 4000 to 8000.

Moreover, the specific gravity of the vinyl group-containing linear organopolysiloxane (A1) is not particularly limited, but is preferably in the range of about 0.9 to 1.1.

By using those having a polymerization degree and a specific gravity in the above ranges, respectively, as the vinyl group-containing linear organopolysiloxane (A1), the improvement of the heat resistance, the flame retardancy, the chemical stability, and the like of the obtained silicone rubber can be promoted.

The vinyl group-containing linear organopolysiloxane (A1) is particularly preferably one having a structure represented by the following formula (1).

[Chem. 5]

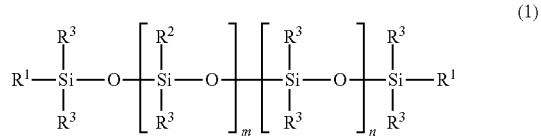

(1)

In the formula (1), $R^1$ is a substituted or unsubstituted alkyl group, alkenyl group, or aryl group having 1 to 10 carbon atoms, or a hydrocarbon group formed by the combination of these groups. Examples of the alkyl group having 1 to 10 carbon atoms include a methyl group, an ethyl group, and a propyl group, and among these, a methyl group is preferred. Examples of the alkenyl group having 1 to 10 carbon atoms include a vinyl group, an allyl group, and a butenyl group, and among these, a vinyl group is preferred. Examples of the aryl group having 1 to 10 carbon atoms include a phenyl group.

Furthermore, $R^2$ is a substituted or unsubstituted alkyl group, alkenyl group, or aryl group having 1 to 10 carbon atoms, or a hydrocarbon group formed by the combination of these groups. Examples of the alkyl group having 1 to 10 carbon atoms include a methyl group, an ethyl group, and a propyl group, and among these, a methyl group is preferred. Examples of the alkenyl group having 1 to 10 carbon atoms include a vinyl group, an allyl group, and a butenyl group, and among these, a vinyl group is preferred. Examples of the aryl group having 1 to 10 carbon atoms include a phenyl group.

Further, $R^3$ is a substituted or unsubstituted alkyl group or aryl group having 1 to 8 carbon atoms, or a hydrocarbon group formed by the combination of these groups. Examples of the alkyl group having 1 to 8 carbon atoms include a methyl group, an ethyl group, and a propyl group, and among these, a methyl group is preferred. Examples of the aryl group having 1 to 8 carbon atoms include a phenyl group.

Furthermore, in the formula (1), examples of the substituent of $R^1$ and $R^2$ include a methyl group and a vinyl group, and examples of the substituent of $R^3$ include a methyl group.

Furthermore, in the formula (1), plural $R^1$s are independent of each other, and may be the same as or different from each other. Further, this shall apply for $R^2$ and $R^3$.

In addition, m and n are each the number of repeating units constituting the vinyl group-containing linear organopolysiloxane (A1) represented by the formula (1), m is an integer of 1 to 1000, and n is an integer of 3000 to 10000. m is preferably from 40 to 700, and n is preferably from 3600 to 8000.

Furthermore, examples of the specific structure of the vinyl group-containing linear organopolysiloxane (A1) represented by the formula (1) include those represented by the following formula (1-1).

[Chem. 6]

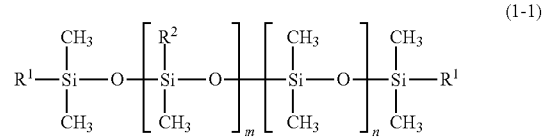

(1-1)

In the formula (1-1), $R^1$ and $R^2$ are each independently a methyl group or a vinyl group, and at least one thereof is a vinyl group.

Furthermore, the vinyl group-containing linear organopolysiloxane (A1) as described above preferably contains a first vinyl group-containing linear organopolysiloxane (A1-1) having a content of the vinyl groups of 0.05% by mole to 0.2% by mole and a second vinyl group-containing linear organopolysiloxane (A1-2) having a content of the vinyl groups of 0.5% by mole to 12% by mole. By combining the first vinyl group-containing linear organopolysiloxane (A1-1) having a general content of the vinyl groups and a second vinyl group-containing linear organopolysiloxane (A1-2) having a high content of the vinyl groups as a raw rubber that is a starting material of a silicone rubber, the vinyl groups can be unevenly distributed, and a higher crosslink density can be effectively formed in the crosslinked network of the silicone rubber. As a result, the tear strength of the silicone rubber can be increased more effectively.

Specifically, it is preferable to use, for example, a first vinyl group-containing linear organopolysiloxane (A1-1) containing 0.05% by mole to 0.2% by mole of the units in which $R^1$ is a vinyl group and/or the units in which $R^2$ is a vinyl group in the formula (1-1), and a second vinyl group-containing linear organopolysiloxane (A1-2) containing 0.5% by mole to 12% by mole of the units in which $R^1$ is a vinyl group and/or the units in which $R^2$ is a vinyl group in the formula (1-1), as the vinyl group-containing linear organopolysiloxane (A1).

Furthermore, the content of the vinyl groups of the first vinyl group-containing linear organopolysiloxane (A1-1) is preferably from 0.1% by mole to 0.15% by mole. Further, the content of the vinyl groups of the second vinyl group-containing linear organopolysiloxane (A1-2) is preferably from 0.8% by mole to 8.0% by mole.

Incidentally, in the case of combining and blending the first vinyl group-containing linear organopolysiloxane (A1-1) and the second vinyl group-containing linear organopolysiloxane (A1-2), the ratio of (A1-1) to (A1-2) is not particularly limited, but (A1-1):(A1-2) is usually preferably from 1:0.05 to 1:0.6, and more preferably from 1:0.08 to 1:0.5, in terms of a weight ratio.

In addition, each of the first and second vinyl group-containing linear organopolysiloxanes (A1-1) and (A1-2) may be used singly or in combination of two or more kinds thereof.

<<Organohydrogen Polysiloxane (B)>>

The organohydrogen polysiloxane (B) is classified into a linear organohydrogen polysiloxane having a linear structure (B1) and a branched organohydrogen polysiloxane having a branched structure (B2), and both of them are used in the present invention.

The linear organohydrogen polysiloxane (B1) is a polymer which has a linear structure, further has a structure in which hydrogen is directly bonded to Si($\equiv$Si—H), and undergoes a hydrosilylation reaction with a vinyl group contained in the components to be blended in the silicone rubber-based curable composition, other than the vinyl group of the vinyl group-containing organopolysiloxane (A), thereby crosslinking these components.

The molecular weight of the linear organohydrogen polysiloxane (B1) is not particularly limited, but the weight average molecular weight is preferably 20000 or less, and more preferably from 1000 to 10000.

Furthermore, the weight average molecular weight of the linear organohydrogen polysiloxane (B1) can be measured by means of GPC (gel permeation chromatography).

Further, typically, the linear organohydrogen polysiloxane (B1) preferably has no vinyl group, whereby the crosslinking reaction can be apparently prevented from proceeding in the molecule of the linear organohydrogen polysiloxane (B1).

As such a linear organohydrogen polysiloxane (B1), for example, one having a structure represented by the following formula (2) is preferably used.

[Chem. 7]

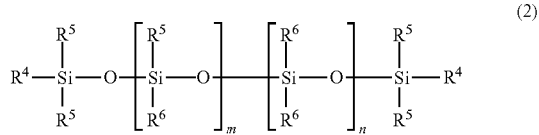

(2)

In the formula (2), $R^4$ is a substituted or unsubstituted alkyl group, alkenyl group, or aryl group having 1 to 10 carbon atoms, a hydrocarbon group formed by the combination of these groups, or a hydride group. Examples of the alkyl group having 1 to 10 carbon atoms include a methyl group, an ethyl group, and a propyl group, and among these, a methyl group is preferred. Examples of the alkenyl group having 1 to 10 carbon atoms include a vinyl group, an allyl group, and a butenyl group, and among these, a vinyl group is preferred. Examples of the aryl group having 1 to 10 carbon atoms include a phenyl group.

Further, $R^5$ is a substituted or unsubstituted alkyl group, alkenyl group, or aryl group having 1 to 10 carbon atoms, a hydrocarbon group formed by the combination of these groups, or a hydride group. Examples of the alkyl group having 1 to 10 carbon atoms include a methyl group, an ethyl group, and a propyl group, and among these, a methyl group is preferred. Examples of the alkenyl group having 1 to 10 carbon atoms include a vinyl group, an allyl group, and a butenyl group, and among these, a vinyl group is preferred. Examples of the aryl group having 1 to 10 carbon atoms include a phenyl group.

Moreover, in the formula (2), plural $R^4$s are independent of each other, and may be the same as or different from each other. Further, this shall apply for $R^5$. However, at least two or more out of plural $R^4$s and $R^5$s are hydride groups.

Further, $R^6$ is a substituted or unsubstituted alkyl group or aryl group having 1 to 8 carbon atoms, or a hydrocarbon group formed by the combination of these groups. Examples of the alkyl group having 1 to 8 carbon atoms include a methyl group, an ethyl group, and a propyl group, and among these, a methyl group is preferred. Examples of the aryl group having 1 to 8 carbon atoms include a phenyl group. Plural $R^6$s are independent of each other, and may be the same as or different from each other.

Furthermore, in the formula (2), examples of the substituent of $R^4$, $R^5$, and $R^6$ include a methyl group and a vinyl group, and a methyl group is preferred from the viewpoint of preventing the crosslinking reaction in the molecule.

In addition, m and n are each the number of repeating units constituting the linear organohydrogen polysiloxane (B1) represented by the formula (2), m is an integer of 0 to 300 and n is an integer of (300-m). Preferably, m is an integer of 0 to 150, and n is an integer of (150-m).

Furthermore, the linear organohydrogen polysiloxanes (B1) may be used singly or in combination of two or more kinds thereof.

The branched organohydrogen polysiloxane (B2) is a component, which has a branched structure, thereby forming an area having a high crosslink density, and greatly contributes to formation of a structure having a high crosslink density in a system of a silicone rubber. Further, in a similar manner to the linear organohydrogen polysiloxane (B1), the branched organohydrogen polysiloxane (B2) is a polymer which has a structure in which hydrogen is directly bonded to Si ($\equiv$Si—H), and undergoes a hydrosilylation reaction with a vinyl group to be blended in the silicone rubber-based curable composition, other than the vinyl group of the vinyl group-containing organopolysiloxane (A), thereby crosslinking these components.

Further, the specific gravity of the branched organohydrogen polysiloxane (B2) is in the range of 0.9 to 0.95.

Furthermore, typically, the branched organohydrogen polysiloxane (B2) preferably has no vinyl group, whereby the crosslinking reaction can be apparently prevented from proceeding in the molecule of the branched organohydrogen polysiloxane (B2).

Furthermore, the branched organohydrogen polysiloxane (B2) is preferably represented by the following average composition formula (c).

Average composition formula (c)

$(H_a(R^7)_{3-a}SiO_{1/2})_m(SiO_{4/2})_n$ (in the formula (c), $R^7$ is a monovalent organic group, a is an integer in the range of 1 to 3, m is the number of $H_a(R^7)_{3-a}SiO_{1/2}$ units, and n is the number of $SiO_{4/2}$ units).

In the formula (c), $R^7$ is a monovalent organic group, and preferably a substituted or unsubstituted alkyl group or aryl group having 1 to 10 carbon atoms, or a hydrocarbon group formed by the combination of these groups. Examples of the alkyl group having 1 to 10 carbon atoms include a methyl group, an ethyl group, and a propyl group, and among these, a methyl group is preferred. Examples of the aryl group having 1 to 10 carbon atoms include a phenyl group.

In the formula (c), a is the number of hydride groups (hydrogen atoms directly bonded to Si), and is an integer in the range of 1 to 3, and preferably 1.

Furthermore, in the formula (c), m is the number of $H_a(R^7)_{3-a}SiO_{1/2}$ units, and n is the number of $SiO_{4/2}$ units.

The branched organohydrogen polysiloxane (B2) has a branched structure. The linear organohydrogen polysiloxane (B1) and the branched organohydrogen polysiloxane (B2) are different in that the structures are linear and branched, respectively, and when the number of Si is 1, the number of the alkyl groups R's bonded to Si (R/Si) is from 1.8 to 2.1 for the linear organohydrogen polysiloxane (B1), or from 0.8 to 1.7 for the branched organohydrogen polysiloxane (B2).

Moreover, since the branched organohydrogen polysiloxane (B2) has a branched structure, for example, when it is heated to 1000° C. at a rate of temperature increase of 10° C./minute under a nitrogen atmosphere, the amount of the residues is 5% or more. On the other hand, since the linear organohydrogen polysiloxane (B1) is linear, the amount of the residues after heating under the above conditions is almost zero.

Moreover, specific examples of the branched organohydrogen polysiloxane (B2) include those having structures represented by the following formula (3).

[Chem. 8]

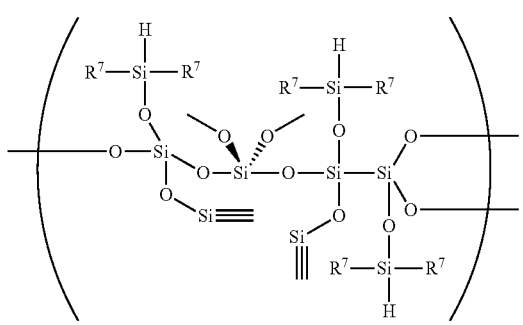

(3)

In the formula (3). $R^7$ a substituted or unsubstituted alkyl group or aryl group having 1 to 8 carbon atoms, or a hydrocarbon group formed by the combination of these groups, or a hydrogen atom. Examples of the alkyl group having 1 to 8 carbon atoms include a methyl group, an ethyl group, and a propyl group, and among these, a methyl group is preferred. Examples of the aryl group having 1 to 8 carbon atoms include a phenyl group. Examples of the substituent of $R^7$ include a methyl group.

Furthermore, in the formula (3), plural $R^7$s are independent of each other, and may be the same as or different from each other.

Further, in the formula (3), "—O—Si≡" denotes that it has a branched structure having Si diffused three-dimensionally.

Incidentally, the branched organohydrogen polysiloxanes (B2) may be used singly or in combination of two or more kinds thereof.

Moreover, in the linear organohydrogen polysiloxane (B1) and the branched organohydrogen polysiloxane (B2), the amount of the hydrogen atoms (hydride groups) directly bonded to Si is not particularly limited. However, in the silicone rubber-based curable composition, the total amount of the hydride groups in the linear organohydrogen polysiloxane (B1) and the branched organohydrogen polysiloxane (B2) is preferably from 0.5 to 5 moles, and more preferably from 1 to 3.5 moles, with respect to one mole of the vinyl groups in the vinyl group-containing linear organopolysiloxane (A1), which ensures a crosslinked network being formed among the linear organohydrogen polysiloxane (B1), the branched organohydrogen polysiloxane (B2), and the vinyl group-containing linear organopolysiloxane (A1).

In addition, with regard to the linear organohydrogen polysiloxane (B1) and the branched organohydrogen polysiloxane (B2), the linear organohydrogen polysiloxane (B1) is included as a main component in the silicone rubber-based curable composition, and the branched organohydrogen polysiloxane (B2) is added when an area having a high crosslink density in the silicone rubber is formed as described above. Accordingly, in the case of combining and blending the linear organohydrogen polysiloxane (B1) and the branched organohydrogen polysiloxane (B2), the ratio of (B1) to (B2), (B1):(B2), is set to preferably from 1:0.1 to 1:1, and more preferably from 1:0.2 to 1:0.5, in terms of a weight ratio.

<<Silica Particles (C)>>

The silica particles (C) are components to be added for the purpose of improving the hardness and the mechanical strength, in particular, the tensile strength of the silicone rubber thus formed.

The specific surface area of the silica particles (C) is preferably from about 50 m²/g to 400 m²/g, and more preferably from about 100 m²/g to 400 m²/g. Further, the average particle diameter is preferably from about 1 nm to 100 nm, and more preferably from about 5 nm to 20 nm.

By using those having the specific surface area and the average particle diameter in the above range as the silica particles (C), the function as the above-described silica particles (C) can be remarkably exhibited.

The silica particles (C) are not particularly limited, but examples thereof include fumed silica, sintered silica, and precipitated silica.

Furthermore, the silica particles (C) may be used singly or in combination of two or more kinds thereof.

<<Silane Coupling Agent (D)>>

In the present invention, the silane coupling agent (D) has a hydrolyzable group. The hydrolyzable group is hydrolyzed to become a hydroxyl group, and the hydroxyl group undergoes a dehydrative condensation reaction with a hydroxyl group on the surface of the silica particles (C) to carry out the surface modification of the silica particles (C).

Moreover, the silane coupling agent (D) has a hydrophobic group. Thus, the hydrophobic group is provided on the surface of the silica particles (C), and accordingly, the aggregation force of the silica particles (C) is reduced (aggregation by hydrogen bonding due to silanol groups is reduced) in the silicone rubber-based curable composition, or further in the silicone rubber. As a result, it is presumed that the dispersibility of the silica particles in the composition is improved. Thus, the interface between the silica particles and the rubber matrix is increased and the reinforcing effect of the silica particles is enhanced. Further, when the matrix modification of the rubber is carried out, the slip properties of the silica particles in the matrix are improved. In addition, due to the improvement of the dispersibility of the silica particles and the improvement of the slip properties, the mechanical strength (for example, tensile strength and tear strength) of the silicone rubber due to the silica particles is improved.

Moreover, the silane coupling agent (D) preferably has a vinyl group. Accordingly, the vinyl group is introduced onto the surface of the silica particles (C). As a result, when the silicone rubber-based curable composition is cured, that is, when a vinyl group contained in the vinyl group-containing organopolysiloxane (A) and a hydride group contained in the organohydrogen polysiloxane (B) undergo a hydrosilylation reaction, thereby forming a network (crosslinked structure), and are thus involved in the hydrosilylation reaction between a vinyl group contained in the silica particles (C) and a hydride group contained in the organohydrogen polysiloxane (B), the silica particles (C) are thereby captured in the network. Thus, a high hardness and a high modulus of the silicone rubber thus formed are promoted.

Here, the silicone rubber as a material of the catheter for medical use is required to have a certain degree of hardness. For example, a catheter formed from a material having a low hardness easily causes problems, for example, generation of deformation by insertion resistance upon insertion into a target site (for example, thoracic cavity) (there is no so-called waist), low kink resistance, and generation of obstruction. To the contrary, by promoting a high hardness, a high modulus, and a high restorability (high rubber elasticity) of the silicone rubber, a catheter formed from the silicone rubber solves the above-described problem.

Examples of the silane coupling agent (D) include those represented by the following formula (4).

$$Y_n\text{—Si—}(OR)_{4-n} \quad (4)$$

In the formula (4), n represents an integer of 1 to 3. Y represents any functional group having a hydrophobic group, a hydrophilic group, or a vinyl group, when n is 1, Y is a hydrophobic group, and when n is 2 or 3, at least one thereof is a hydrophobic group. OR represents a hydrolyzable group.

The hydrophobic group is an alkyl group or aryl group having 1 to 6 carbon atoms, or a hydrocarbon group formed by the combination of these groups, and examples thereof include a methyl group, an ethyl group, a propyl group, and a phenyl group, and among these, in particular, a methyl group is preferred.

Furthermore, examples of the hydrophilic group include a hydroxyl group, a sulfonic acid group, a carboxyl group, and a carbonyl group, and among these, in particular, a hydroxyl group is preferred. Further, the hydrophilic group may be contained as a functional group, but is preferably not contained from the viewpoint of providing hydrophobicity to the silane coupling agent (D).

Furthermore, examples of the hydrolyzable group include alkoxy groups such as a methoxy group and an ethoxy group, a chloro group, and a silazane group, and among these, the silazane group is preferred from the viewpoint of high reactivity with the silica particles (C). In addition, the incorporation of a silazane group as the hydrolyzable group means the incorporation of a structure of $(Y_n\text{—Si—})$ in the formula (4) from its structural characteristics.

Specific examples of the silane coupling agent (D) represented by the formula (4) include those having a hydrophobic group as a functional group, for example, alkoxysilanes such as methyltrimethoxysilane, dimethyldimethoxysilane, phenyltrimethoxysilane, methyltriethoxysilane, dimethyldiethoxysilane, phenyltriethoxysilane, n-propyltrimethoxysilane, n-propyltriethoxysilane, hexyltrimethoxysilane, hexyltriethoxysilane, and decyltrimethoxysilane; chlorosilanes such as methyltrichlorosilane, dimethyldichlorosilane, trimethylchlorosilane, and phenyltrichlorosilane; and hexamethyldisilazane; and those having a vinyl group as a functional group, for example, alkoxysilanes such as methacryloxypropyltriethoxysilane, methacryloxypropyltrimethoxysilane, methacryloxypropylmethyldiethoxysilane, methacryloxypropylmethyldimethoxysilane, vinyltriethoxysilane, vinyltrimethoxysilane, and vinylmethyldimethoxysilane; chlorosilanes such as vinyltrichlorosilane, and vinylmethyldichlorosilane; and divinyltetramethyldisilazane, and among these, in consideration of the description above, particularly, as the silane coupling agent (D) having a hydrophobic group, hexamethyldisilazane is preferred; and as the silane coupling agent (D) having a vinyl group, divinyltetramethyldisilazane is preferred.

<<Platinum or Platinum Compound (E)>>

The platinum or platinum compound (E) is a compound that acts as a catalyst during the curing, and its addition amount is a catalytic amount.

As the platinum or platinum compound (E), known ones can be used, and examples thereof include platinum black, those having platinum supported on silica, carbon black, or the like, chloroplatinic acid or an alcohol solution of chloroplatinic acid, a complex salt of chloroplatinic acid with an olefin, and a complex salt of chloroplatinic acid with vinyl siloxane.

In addition, the platinum or platinum compound (E) that is a catalyst component may be used singly or in combination of two or more kinds thereof.

<<Water (F)>>

Moreover, the silicone rubber-based curable composition of the present invention may further include water (F), in addition to the components (A) to (E).

Water (F) is a component that functions as a dispersion medium for dispersing the respective components included in the silicone rubber-based curable composition and contributes to the reaction of the silica particles (C) with the silane coupling agent (D).

Furthermore, the silicone rubber-based curable composition of the present invention may include known components to be blended in the silicone rubber-based curable composition, in addition to the components (A) to (F). Examples of the known components include diatomaceous earth, iron oxide, zinc oxide, titanium oxide, barium oxide, magnesium oxide, cerium oxide, calcium carbonate, magnesium carbonate, zinc carbonate, glass wool, and mica. In addition, a dispersing agent, a pigment, a dye, an antistatic agent, an antioxidant, a flame retardant, a thermal conductivity enhancing agent, or the like may be appropriately blended.

In addition, the contents of the respective components in the silicone rubber-based curable composition is not particularly limited, but is set in the following manner, for example.

That is, with regard to the silica particles (C), the silica particles (C) are preferably contained in a proportion of 10 parts by weight to 100 parts by weight, and more preferably in a proportion of 35 parts by weight to 75 parts by weight, with respect to 100 parts by weight of the total amount of (A) and (B), which can ensure the tensile strength of the silicone rubber being improved to a desired range.

With regard to the silane coupling agent (D), the silane coupling agent (D) is preferably contained in a proportion of 5 parts by weight to 100 parts by weight, and more preferably in a proportion of 10 parts by weight to 40 parts by weight, with respect to 100 parts by weight of the silica particles (C), which can ensure the dispersibility of the silica particles (C) in the silicone rubber-based curable composition being improved.

The content of the platinum or platinum compound (E) means a catalytic amount and may be set appropriately, but specifically, the content is preferably in the range of 0.01 parts by weight to 5 parts by weight, and more preferably in the range of 0.02 parts by weight to 0.2 parts by weight, with respect to 100 parts by weight of the total amount of (A) and (B), which can ensure a reaction between the vinyl group-containing organopolysiloxane (A) and the organohydrogen polysiloxane (B) proceeding.

Furthermore, in the case where water (F) is included, the content thereof can be set appropriately, but specifically, it is preferably in the range of 10 parts by weight to 100 parts by weight, and more preferably in the range of 30 parts by weight to 70 parts by weight, with respect to 100 parts by weight of the silane coupling agent (D), which can ensure a reaction between the silane coupling agent (D) and the silica particles (C) proceeding.

Since the silicone rubber-based curable composition having such a configuration includes the silica particles (C) and the silane coupling agent (D) as described above, the surface modification of the silica particles (C) with the silane coupling agent (D) proceeds in the silicone rubber-based curable composition. Accordingly, the dispersibility of the silica particles (C) in the silicone rubber-based curable composition is improved stepwise, which is presumed to improve the strength (particularly, tensile strength and tear strength) of a silicone rubber obtained by curing the silicone rubber-based curable composition.

The silicone rubber-based curable composition and the silicone rubber, each having such a configuration, are produced in the following manner, for example.

Hereinafter, a case where a silicone rubber-based curable composition is prepared, and then the silicone rubber-based curable composition is cured to produce a silicone rubber will be described.

<Method for Producing Silicone Rubber>

The silicone rubber can be obtained by preparing the respective components as described above, uniformly mixing them by an arbitrary kneading device to prepare a silicone rubber-based curable composition, and then heating and curing the silicone rubber-based curable composition, but a silicone rubber having excellent strength can be obtained through the preparation using the steps as shown below.

[1] First, the vinyl group-containing organopolysiloxane (A), the silica particles (C), and the silane coupling agent (D) are weighed to predetermined amounts, and then kneaded using an arbitrary kneading device, thereby obtaining a kneaded product containing these respective components (A), (C), and (D).

Further, this kneaded product is preferably obtained by kneading the vinyl group-containing organopolysiloxane (A) with the silane coupling agent (D) in advance, and then kneading (mixing) them with the silica particles (C). Thus, the dispersibility of the silica particles (C) in the vinyl group-containing organopolysiloxane (A) is further improved.

Incidentally, when this kneaded product is obtained, water (F) may be added, if necessary, to the respective components (A), (C), and (D).

In addition, it is preferable to knead the components (A), (C), and (D)) by conducting a first step of heating the components to a first temperature and a second step of heating the components to a second temperature. Thus, in the first step, the surface of the silica particles (C) can be treated with the coupling agent (D), and in the second step, removal from the kneaded product of the by-products that are produced in the reaction of the silica particles (C) with the coupling agent (D) is ensured.

The first temperature is preferably from about 40° C. to 120° C., and more preferably from about 60° C. to 90° C. The second temperature is preferably from about 130° C. to 210° C., and more preferably from about 160° C. to 180° C.

Further, the atmosphere in the first step is preferably an inert atmosphere such as a nitrogen atmosphere, and the atmosphere in the second step is preferably an atmosphere under reduced pressure.

Furthermore, the time in the first step is preferably from about 0.3 hours to 1.5 hours, and more preferably from about 0.5 hours to 1.2 hours. The time in the second step is preferably from about 0.7 hours to 3.0 hours, and more preferably from about 1.0 hour to 2.0 hours.

By conducting the first step and the second step under the same conditions, the effects above can be obtained more apparently.

[2] Then, the organohydrogen polysiloxane (B) and the platinum or platinum compound (E) are weighed to predetermined amounts, and then the kneaded product prepared in the step [1] is kneaded with the respective components (B) and (E) using an arbitrary kneading device, thereby obtaining a silicone rubber-based curable composition.

Furthermore, when the respective components (B) and (E) are kneaded, it is preferable to knead the organohydrogen polysiloxane (B) with the kneaded product prepared in the step [1] and knead the platinum or platinum compound (E) with the kneaded product prepared in the step [1]) in advance; and then knead the respective kneaded products obtained above. As a result, dispersal of the respective components (A) to (E) is ensured in the silicone rubber-based curable composition without the progress of the reaction between the vinyl group-containing organopolysiloxane (A) and the organohydrogen polysiloxane (B).

The temperature at which the respective components (B) and (E) are kneaded, which is a roll setting temperature, is preferably from about 10° C. to 70° C., and more preferably from about 25° C. to 30° C.

In addition, the kneading time is preferably from about 5 minutes to 1 hour, and more preferably from about 10 minutes to 40 minutes.

By adopting such a temperature range, it is possible to prevent or inhibit the progress of the reaction between the vinyl group-containing organopolysiloxane (A) and the organohydrogen polysiloxane (B) more apparently, and further, by adopting a kneading time in such a range, it is further ensured that the respective components (A) to (E) be dispersed in the silicone rubber-based curable composition.

Furthermore, the kneading device used in each of the steps [1] and [2] is not particularly limited, but for example, a kneader, 2 rolls, a Banbury mixer (continuous kneader), a pressurization kneader, or the like may be used.

Moreover, in the present step [2], a reaction inhibitor such as 1-ethynylcyclohexanol may also be added to the kneaded product. Thus, even though the temperature of the kneaded product is set to a relatively high temperature, it is possible to prevent or inhibit the progress of the reaction between the vinyl group-containing organopolysiloxane (A) and the organohydrogen polysiloxane (B) more apparently.

[3] Then, a silicone rubber is formed by curing the silicone rubber-based curable composition.

Curing of the silicone rubber-based curable resin composition is carried out, for example, by heating at 140° C. to 180° C. for 5 minutes to 15 minutes (first curing) and then post-baking at 200° C. for 4 hours (second curing).

By conducting the steps as described above, a silicone rubber is obtained.

Moreover, a molded article having excellent mechanical strength can be obtained by using the silicone rubber as described above.

In addition, a tube for medical use (for example, catheter) made from a silicone rubber, having excellent kink resistance, scratch resistance, and insertability, can be obtained by using such a molded article.

The kink resistance is involved with the tensile strength and the hardness, and the insertability is involved with the tensile strength.

The silicone rubber-based curable composition, the molded article, and the tube for medical use of the present invention are described above, but the present invention is not intended to be limited thereto.

For example, arbitrary components that can perform the same functions may be added to the silicone rubber-based curable composition, the molded article, and the tube for medical use of the present invention.

Next, in a second embodiment of the present invention, the silicone rubber-based curable composition, the molded article, and the tube for medical use will be described, based on a suitable embodiment. What is not mentioned in the present embodiment is the same as in the first embodiment of the present invention.

<Silicone Rubber-Based Curable Composition>

First, the silicone rubber-based curable composition of the present embodiment will be described.

The silicone rubber-based curable composition of the present embodiment includes a vinyl group-containing organopolysiloxane (A), an organohydrogen polysiloxane (B), silica particles (C), a silane coupling agent (D), and platinum or a platinum compound (E), and includes both of a linear organohydrogen polysiloxane having a linear structure (B1) and a branched organohydrogen polysiloxane having a branched structure (B2) as the organohydrogen polysiloxane (B).

<<Organohydrogen Polysiloxane (B)>>

The organohydrogen polysiloxane (B) is classified into a linear organohydrogen polysiloxane having a linear structure (B1) and a branched organohydrogen polysiloxane having a branched structure (B2), and in the present embodiment both of the linear organohydrogen polysiloxane (B1) and the branched organohydrogen polysiloxane (B2) are included in the silicone rubber-based curable composition.

By including both of the linear organohydrogen polysiloxane (B1) and the branched organohydrogen polysiloxane (B2) as the organohydrogen polysiloxane (B) as described above, an area having a high crosslink density and an area having a low crosslink density are formed in the silicone rubber. That is, a structure having different crosslink densities in the system is formed. As a result, the silicone rubber obtained has excellent tensile strength and tear strength as well as a low compression permanent strain. Accordingly, for example, a catheter formed using such a silicone rubber is hardly deformed due to a cause of insertion resistance upon insertion into a target site (for example, thoracic cavity) (there is a so-called waist) and has excellent low kink resistance.

Moreover, a smaller value of compression permanent strain denotes superior rubber elasticity, and is an index indicative of a restoring force that gives an important effect to the kink resistance of a catheter (tube molded article) formed using such a silicone rubber.

Furthermore, in the linear organohydrogen polysiloxane (B1) and the branched organohydrogen polysiloxane (B2), the amount of the hydrogen atoms (hydride groups) directly bonded to Si is not particularly limited. However, in the silicone rubber-based curable composition, the total amount of the hydride groups in the linear organohydrogen polysiloxane (B1) and the branched organohydrogen polysiloxane (B2) is preferably from 0.5 moles to 5 moles, and more preferably from 1 mole to 3.5 moles, with respect to one mole of the vinyl groups in the vinyl group-containing linear organopolysiloxane (A1), which can ensure a crosslinked network among the linear organohydrogen polysiloxane (B1), the branched organohydrogen polysiloxane (B2), and the vinyl group-containing linear organopolysiloxane (A1) being formed.

Furthermore, with regard to the linear organohydrogen polysiloxane (B1) and the branched organohydrogen polysiloxane (B2), typically, the linear organohydrogen polysiloxane (B1) is included as a main component in the silicone rubber-based curable composition, and the branched organohydrogen polysiloxane (B2) is added so as to form an area having a high crosslink density in the silicone rubber as described above. Accordingly, the ratio of the linear organohydrogen polysiloxane (B1) to the branched organohydrogen polysiloxane (B2), (B1) to (B2), is set to preferably from 1:0.1 to 0.8, and more preferably from 1:0.2 to 1:0.4, in terms of a weight ratio.

It is presumed that since both of the linear organohydrogen polysiloxane (B1) and the branched organohydrogen polysiloxane (B2) are included as the organohydrogen polysiloxane (B), a dense structure having different crosslink densities is formed in the silicone rubber system, and as a result, the tensile strength and the tear strength of the obtained silicone rubber are improved and the compression permanent strain is low.

Moreover, it is possible obtain a molded article having excellent mechanical strength and a low compression permanent strain by using such a silicone rubber.

Furthermore, it is possible obtain a tube for medical use (for example, catheter) formed from a silicone rubber having excellent kink resistance, scratch resistance, and insertability by using such a molded article.

In addition, the kink resistance is involved with the tensile strength, the hardness, and the compression permanent strain, and the insertability is involved with the tensile strength.

EXAMPLES

Next, specific Examples of the present invention will be described.

Furthermore, the present invention is not restricted to the description in Examples in any way.

Examples 1 to 10 and Comparative Examples 1 and 2

1. Preparation of Raw Materials

First, the raw materials used in Examples 1 to 10 and Comparative Examples 1 and 2 are shown below.

(1) First Vinyl Group-Containing Linear Organopolysiloxane (A1-1) (content of vinyl groups 0.13% by mole): This was synthesized according to the following synthesis scheme.

(2) Second Vinyl Group-Containing Linear Organopolysiloxane (A1-2) (content of vinyl groups 0.92% by mole): This was synthesized according to the following synthesis scheme.

(3) Linear Organohydrogen Polysiloxane (B1): "88466" manufactured by Momentive Performance Materials Inc. was prepared.

(4) Silica Particles (C-1): Silica fine particles (specific surface area 300 m$^2$/g), "AEROSIL 300" manufactured by Nippon Aerosil Co., Ltd. were prepared.

(5) Silica Particles (C-2): Silica fine particles (specific surface area 200 m$^2$/g), "AEROSIL 200" manufactured by Nippon Aerosil Co., Ltd. were prepared.

(6) Silica Particles (C-3): Silica fine particles (specific surface area 130 m$^2$/g), "AEROSIL 130" manufactured by Nippon Aerosil Co., Ltd. were prepared.

(7) Silane coupling agent (D-1): Hexamethyldisilazane (HMDZ), "HEXAMETHYLDISILAZANE (SIH 6110.1)" manufactured by Gelest was prepared.

(8) Silane Coupling Agent (D-2): Divinyltetramethyldisilazane, "1,3-DIVINYLTETRAMETHYLDISILAZANE (SID4612.0)" manufactured by Gelest was prepared.

(9) Silane Coupling Agent (D-3): Dimethyldichlorosilane, "DIMETHYLDICHLOROSILANE (SID4120.0)" manufactured by Gelest was prepared.

(10) Platinum or Platinum Compound (E): Platinum compound, "PLATINUM DIVINYLTETRAMETHYLDISILOXANE COMPLEX in xylene (SIP6831.2)" manufactured by Gelest was prepared.

Synthesis of First Vinyl Group-Containing Linear Organopolysiloxane (A1-1)

According to the following formula (4), the first vinyl group-containing organopolysiloxane was synthesized.

That is, in a 300 mL separable flask having a condenser and a stirring blade, which was purged with Ar gas, were placed 74.7 g (252 mmol) of octamethylcyclotetrasiloxane, 0.086 g (0.25 mmol) of 2,4,6,8-tetramethyl-2,4,6,8-tetravinylcyclotetrasiloxane, and 0.1 g of potassium siliconate, and the mixture was warmed and stirred at 120° C. for 30 minutes. Further, at this time, it could be seen that the viscosity was increased.

Thereafter, the mixture was warmed to 155° C. and continued to be stirred for 3 hours. Further, after 3 hours. 0.1 g (0.6 mmol) of 1,3-divinyltetramethyldisiloxane was added thereto, followed by further stirring at 155° C. for 4 hours.

Further, after 4 hours, the mixture was diluted with 250 mL of toluene and then washed with water three times. The organic layer after washing was washed with 1.5 L of methanol several times and purified by reprecipitation, and the oligomer and the polymer were separated. The obtained polymer was dried at 60° C. overnight under reduced pressure to obtain a first vinyl group-containing linear organopolysiloxane (A1-1) (Mn=277,734, Mw=573,906, IV value (dl/g)=0.89).

[Chem. 9]

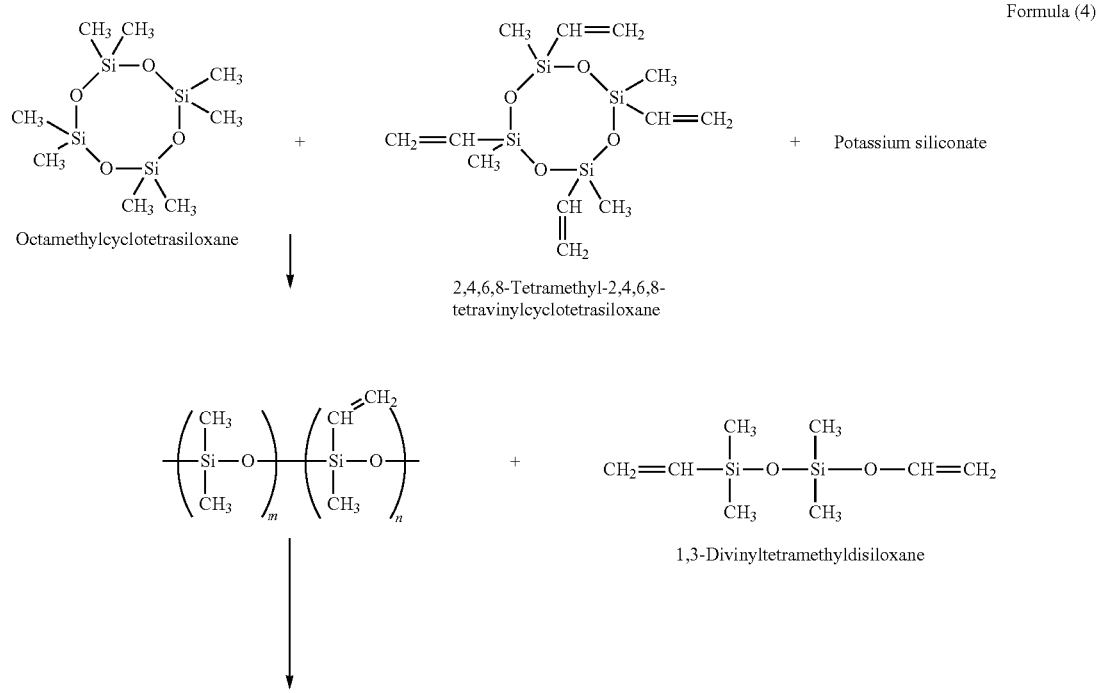

Formula (4)

-continued

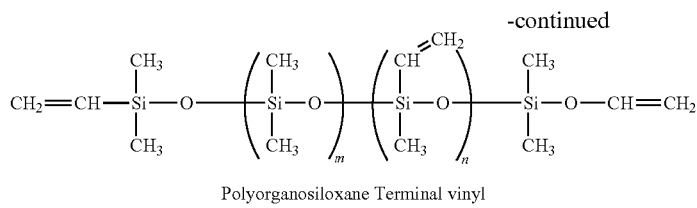

Polyorganosiloxane Terminal vinyl

Synthesis of Second Vinyl Group-Containing Linear Organopolysiloxane (A1-2)

In the same manner as described above except that 2,4,6,8-tetramethyl-2,4,6,8-tetravinylcyclotetrasiloxane was used in the amount of 0.86 g (2.5 mmol) in the synthesis of (A1-1), a second vinyl group-containing organopolysiloxane (A1-2) was synthesized.

2. Preparation of Silicone Rubber-Based Curable Composition

Example 1

First, 100 parts by weight of a vinyl group-containing linear organopolysiloxane (A1) [(A1-1):(A1-2)=80 parts by weight:20 parts by weight] was kneaded with 10 parts by weight of hexamethyldisilazane (D-1), 0.5 parts by weight of divinyltetramethyldisilazane (D-2), and 5.25 parts by weight of water (F) in advance, and then 60 parts by weight of silica particles (C-1) was added thereto, followed by kneading them, to obtain a kneaded product (silicone rubber compound).

Further, the kneading after the addition of the silica particles (C-1) was carried out for a coupling reaction by conducting a first step of kneading for 1 hour under the condition of 60 to 90° C. under a nitrogen atmosphere and a second step of kneading for 2 hours under the condition of 160° C. to 180° C. so as to remove the by-product (ammonia) under reduced pressure.

In addition, the obtained kneaded product was cooled to room temperature.

Then, to this kneaded product were added 0.46 parts by weight of the linear organohydrogen polysiloxane (B1) and 0.05 parts by weight of the platinum compound (E), followed by kneading them by a roll, to obtain a silicone rubber-based curable composition.

Example 2

In the same manner as in Example I except that the linear organohydrogen polysiloxane (B1) and the silica particles (C-1) were charged in the amounts of 0.53 parts by weight and 65 parts by weight, respectively, a silicone rubber-based curable composition was prepared.

Example 3

In the same manner as in Example 1 except that the linear organohydrogen polysiloxane (B1) and the silica particles (C-1) were charged in the amounts of 0.70 parts by weight and 70 parts by weight, respectively, a silicone rubber-based curable composition was prepared.

Example 4

First, 100 parts by weight of a vinyl group-containing linear organopolysiloxane (A1) [(A1-1):(A1-2)=80 parts by weight:20 parts by weight] was kneaded with 10.5 parts by weight of hexamethyldisilazane (D-1) and 5.25 parts by weight of water (F) in advance, and then 45 parts by weight of silica particles (C-1) was added thereto, followed by kneading them, to obtain a kneaded product (silicone rubber compound).

Further, the kneading after the addition of the silica particles (C-1) was carried out for a coupling reaction by conducting a first step of kneading for 1 hour under the condition of 60° C. to 90° C. under a nitrogen atmosphere and a second step of kneading for 2 hours under the condition of 160° C. to 180° C. so as to remove the by-product (ammonia) under reduced pressure.

In addition, the obtained kneaded product was cooled to room temperature.

Then, to this kneaded product were added 0.41 parts by weight of the linear organohydrogen polysiloxane (B1) and 0.05 parts by weight of the platinum compound (E), followed by kneading them by a roll, to obtain a silicone rubber-based curable composition.

Example 5

In the same manner as in Example 4 except that the linear organohydrogen polysiloxane (B1) and the silica particles (C-1) were charged in the amounts of 0.39 parts by weight and 50 parts by weight, respectively, a silicone rubber-based curable composition was prepared.

Example 6

In the same manner as in Example 4 except that the linear organohydrogen polysiloxane (B1) and the silica particles (C-1) were charged in the amounts of 0.48 parts by weight and 55 parts by weight, respectively, a silicone rubber-based curable composition was prepared.

Example 7

In the same manner as in Example 4 except that the linear organohydrogen polysiloxane (B1) and the silica particles (C-1) were charged in the amounts of 0.51 parts by weight and 75 parts by weight, respectively, a silicone rubber-based curable composition was prepared.

Example 8

First, 100 parts by weight of a vinyl group-containing linear organopolysiloxane (A1-1) was kneaded with 10.5 parts by weight of dimethyldichlorosilane (D-3) and 5.25 parts by weight of water (F) in advance, and then 50 parts by weight of silica particles (C-2) was added thereto, followed by kneading them, to obtain a kneaded product (silicone rubber compound).

Further, the kneading after the addition of the silica particles (C-2) was carried out for a coupling reaction by conducting a first step of kneading for 1 hour under the condition of 60° C. to 90° C. under a nitrogen atmosphere and a second step of kneading for 2 hours under the condition of 160° C. to 180° C. so as to remove the by-product under reduced pressure.

In addition, the obtained kneaded product was cooled to room temperature.

Then, to this kneaded product were added 2.0 parts by weight of the linear organohydrogen polysiloxane (B1) and 0.05 parts by weight of the platinum compound (E), followed by kneading them by a roll, to obtain a silicone rubber-based curable composition.

Example 9

In the same manner as in Example 8 except that the silica particles (C-2) were charged in the amount of 70 parts by weight, a silicone rubber-based curable composition was prepared.

Example 10

In the same manner as in Example 8 except that the silica particles (C-3) were charged in the amount of 50 parts by weight, a silicone rubber-based curable composition was prepared.

Comparative Example 1

First, to 100 parts by weight of a vinyl group-containing linear organopolysiloxane (A1-1) were added 33 parts by weight of silica particles (C-1), followed by kneading them, to obtain a kneaded product (silicone rubber compound).

Further, the kneading after the addition of the silica particles (C-1) was carried out by kneading at room temperature (27° C.) for 15 minutes.

In addition, the obtained kneaded product was cooled to room temperature.

Then, to this kneaded product were added 2.0 parts by weight of the linear organohydrogen polysiloxane (B1) and 0.05 parts by weight of the platinum (E), followed by kneading them by a roll, to obtain a silicone rubber-based curable composition.

Comparative Example 2

In the same manner as in Comparative Example 1 except that the silica particles (C-2) were charged in the amount of 33 parts by weight, a silicone rubber-based curable composition was prepared.

3. Evaluation

The obtained silicone rubber-based curable composition of each of Examples and Comparative Examples was evaluated by the following method.

3-1. Evaluation of Tensile Strength, Strain, Tear Strength, and Stroke

The silicone rubber-based curable composition of each of Examples and Comparative Examples was pressed at 170° C. and 10 MPa for 10 minutes, and molded into a 1 mm sheet shape, while carrying out a first curing. Subsequently, the composition was heated at 200° C. for 4 hours and subjected to a second curing.

Further, using the obtained silicone rubber in the sheet shape, a dumbbell-shaped #3 type test piece was prepared in accordance with JIS K6251 (2004), a crescent type test piece was prepared in accordance with JIS K6252 (2001), the tensile strength and the strain of the dumbbell-shaped #3 type test piece were measured in accordance with JIS K6251 (2004), and the tear strength and the stroke of the crescent type test piece were measured in accordance with JIS K6252 (2001).

However, the thickness of the test piece used for the measurement of the tensile strength, the strain, the tear strength, and the stroke was set to 1 mm.

3-2. Evaluation of Hardness

For the silicone rubber-based curable composition of each of Examples and Comparative Examples, a silicone rubber in the sheet shape was prepared in the same manner as for the tensile strength, the strain, the tear strength, and the stroke, and the Type A durometer hardness was measured in accordance with JIS K6253 (1997). The thickness of the test piece was set to 6 mm or more by laminating 1 mm sheets.

The evaluation results of the silicone rubber-based curable composition of each of Examples and Comparative Examples obtained as above are shown in Table 1 below, respectively.

TABLE 1

| | Vinyl group-containing linear polyorganosiloxane (A) | | | | Silica particles (C) | | | Silane coupling agent (D) | |
|---|---|---|---|---|---|---|---|---|---|
| | Low vinyl rubber | High vinyl rubber | Linear organohydrogen siloxane (B) | | Specific surface area | Filling amount | Filling amount (% by weight) | Hexamethyldisilazane (D-1) | Tetramethyldivinyldisilazane (D-2) |
| | (parts) | (parts) | (parts) | [H]/[CH$_2$CH] | (m$^2$/g) | (parts) | | (parts) | (parts) |
| Example 1 | 80.0 | 20.0 | 0.46 | 1.25 | 300 | 60 | 34.1 | 10.0 | 0.5 |
| Example 2 | 80.0 | 20.0 | 0.53 | 1.50 | 300 | 65 | 36.0 | 10.0 | 0.5 |
| Example 3 | 80.0 | 20.0 | 0.70 | 2.00 | 300 | 70 | 37.7 | 10.0 | 0.5 |
| Example 4 | 80.0 | 20.0 | 0.41 | 1.00 | 300 | 45 | 28.0 | 10.5 | 0.0 |
| Example 5 | 80.0 | 20.0 | 0.39 | 1.00 | 300 | 50 | 30.2 | 10.5 | 0.0 |
| Example 6 | 80.0 | 20.0 | 0.48 | 1.25 | 300 | 55 | 32.2 | 10.5 | 0.0 |
| Example 7 | 80.0 | 20.0 | 0.51 | 1.50 | 300 | 75 | 39.3 | 10.5 | 0.0 |
| Example 8 | 100.0 | — | 2.0 | — | 200 | 50 | 33.0 | — | — |
| Example 9 | 100.0 | — | 2.0 | — | 200 | 70 | 41.2 | — | — |
| Example 10 | 100.0 | — | 2.0 | — | 130 | 50 | 33.0 | — | — |

TABLE 1-continued

| | | | | | | | | |
|---|---|---|---|---|---|---|---|---|
| Comparative Example 1 | 100.0 | — | 2.0 | — | 200 | 33 | 25.0 | — | — |
| Comparative Example 2 | 100.0 | — | 2.0 | — | 300 | 33 | 25.0 | — | — |

| | Silane coupling agent (D) Dimethyl-dichlorosilane (D-3) (parts) | Crescent JIS K 6252 | | #3 Dumbbell JIS K 6251 | | JIS K 6253 |
|---|---|---|---|---|---|---|
| | | Tear strength | Stroke | Tensile strength | Strain | Hardness |
| Example 1 | — | 51.4 | 275.5 | 7.2 | 1216.6 | 55.4 |
| Example 2 | — | 50.1 | 135.5 | 7.5 | 916.6 | 63.8 |
| Example 3 | — | 49.5 | 91.9 | 8.5 | 820.7 | 70.6 |
| Example 4 | — | 50.7 | 481.1 | 8.8 | 2504.1 | 35.9 |
| Example 5 | — | 50.7 | 507.9 | 7.9 | 2320.7 | 40.1 |
| Example 6 | — | 50.8 | 317.4 | 8.2 | 1662.4 | 45.5 |
| Example 7 | — | 50.2 | 135.5 | 7.4 | 884.4 | 69.0 |
| Example 8 | 10.5 | 21.3 | 43.5 | 10.3 | 993.3 | 65.2 |
| Example 9 | 10.5 | 12.4 | 6.4 | 8.4 | 474.9 | 80.2 |
| Example 10 | 10.5 | 10.9 | 23.3 | 9.2 | 827.3 | 58.2 |
| Comparative Example 1 | — | 13.7 | 15.0 | 5.1 | 572.8 | 72.0 |
| Comparative Example 2 | — | 10.3 | 4.4 | 7.4 | 324.5 | 79.0 |

As shown in Table 1, in Comparative Example 1, an increase in the strength to such an extent that the silica particles (C) as the filler are filled was found, but it could not be said that the tensile strength was sufficient. In order to improve the tensile strength, the tilling amount of the tear strength filler or the specific surface area of the filler was increased. Thus, the interface between the rubber matrix and the silica particles was increased and an increase in the reinforcing effect by the filler could be expected, but with the untreated filler, aggregation among the different types of fillers was strong and it was difficult to charge a higher amount.

Furthermore, in Comparative Example 2 in which the specific surface area of the filler was large, as compared with Comparative Example 1, the reinforcing effect was enhanced and the tensile strength was improved, but the hydrophilicity of the filler surface remained. Thus, when the matrix of the silicone rubber was obtained by curing the silicone rubber-based curable composition, the slip properties of the silica particles in the matrix were poor, and in particular the tear strength was reduced.

To the contrary, in Examples in which the silane coupling agent was included, as compared with Comparative Examples in which the silane coupling agent (D) was not included, since the filler surface is hydrophobic, the aggregation force among the silica particles (C) is reduced, and as a result, it was possible to increase the filling amount of the filler or to increase the specific surface area of the filler. Further, since the filler surface is hydrophobic, during the modification of the matrix of the silicone rubber, the slip properties of the silica particles in the matrix were also improved, and the improvement of dispersibility and slip properties made it possible to improve both types of the mechanical strength of the tensile strength and the tear strength.

Moreover, Examples 1 to 7 showed the result that a silicone rubber having particularly excellent tear strength was obtained, as compared with Examples 8 to 10. This is due to the fact that the hydrophobic group treated on the surface of the silica particles was a dimethylsilyl group in Examples 8 to 10, whereas the hydrophobic group was a trimethylsilyl group in Examples 1 to 7, which provides higher hydrophobicity. As a result, it is thought that the reinforcing effect as described above was more apparently exhibited. In Examples 1 to 7, since the filling amount of the filler was substantially the same as that in Examples 8 to 10, the tensile strength was approximately equivalent, and in particular, the improvement of the tear strength was found. Further, it is presumed that the use of a coupling agent (D) having a silazane group as a hydrolyzable group causes the reaction rate of the coupling agent (D) with the silica particles (C) to be increased.

The details of the mechanism for the improved tear strength are considered as follows. As the dispersibility of the silica particles is improved, the interface between the silica particles and the rubber matrix is increased and the rubber molecule chains under the action of the silica particles are increased. Thus, the reinforcing effect of the silica particles is increased and the mechanical strength is improved. The rubber molecule chains under the action of the silica particles have molecular mobility lowered by interaction with the silica particles and a harder structure than a portion having a high molecular mobility. In the tear behavior of the silicone rubber, if a tear stress is applied to the hard structure upon the growth and propagation of the initial cracks, it acts as a drag, and as a result, the tear strength is increased.

In addition, Examples 1 to 3 showed the results in which a silicone rubber having excellent hardness was obtained, as compared with Examples 4 to 7. This is presumed to be due to the fact that by using the coupling agent (D) having a vinyl group as a functional group, the silica particles (C) are incorporated into a network (crosslinked structure) formed by the reaction of the vinyl group-containing organopolysiloxane (A) with the organohydrogen polysiloxane (B).

Examples 11 to 13 and Reference Examples 1 and 2

1. Preparation of Raw Materials
First, the raw materials used in Examples 11 to 13 and Reference Examples 1 and 2 are shown below.
(1) First Vinyl Group-Containing Linear Organopolysiloxane (A1-1) (content of vinyl groups 0.13% by mole): This was synthesized according to the following synthesis scheme.

(2) Second Vinyl Group-Containing Linear Organopolysiloxane (A1-2) (content of the vinyl groups 0.92% by mole): This was synthesized according to the following synthesis scheme.

(3) Linear Organohydrogen Polysiloxane (B1): "88466" manufactured by Momentive Performance Materials Inc. was prepared.

(4) Branched Organohydrogen Polysiloxane (B2): "HQM-105" manufactured by GELEST was prepared.

(5) Silica Particles (C-1): Silica fine particles (specific surface area 300 m²/g), "AEROSIL 300" manufactured by Nippon Aerosil Co., Ltd. were prepared.

(6) Silane coupling agent (D-1): Hexamethyldisilazane (HMDZ), "HEXAMETHYLDISILAZANE (SIH 6110.1)" manufactured by Gelest was prepared.

(7) Silane Coupling Agent (D-2): Divinyltetramethyldisilazane, "1,3-DIVINYLTETRAMETHYLDISILAZANE (SID4612.0)" manufactured by Gelest was prepared.

(8) Platinum or Platinum Compound (E): Platinum compound, "PLATINUM DIVINYLTETRAMETHYLDISILOXANE COMPLEX in xylene (SIP6831.2)" manufactured by Gelest was prepared.

Synthesis of First Vinyl Group-Containing Linear Organopolysiloxane (A1-1)

According to the following formula (4), the first vinyl group-containing organopolysiloxane was synthesized.

That is, in a 300 mL separable flask having a condenser and a stirring blade, purged with Ar gas, were placed 74.7 g (252 mmol) of octamethylcyclotetrasiloxane. 0.086 g (0.25 mmol) of 2,4,6,8-tetramethyl-2,4,6,8-tetravinylcyclotetrasiloxane, and 0.1 g of potassium siliconate, and the mixture was warmed and stirred at 120° C. for 30 minutes. Further, at this time, it could be seen that the viscosity was increased.

Thereafter, the mixture was warmed to 155° C. and continued to be stirred for 3 hours. Further, after 3 hours, 0.1 g (0.6 mmol) of 1,3-divinyltetramethyldisiloxane was added thereto, followed by further stirring at 155° C. for 4 hours.

Further, after 4 hours, the mixture was diluted with 250 mL of toluene and then washed with water three times. The organic layer after washing was washed with 1.5 L of methanol several times, and purified by reprecipitation, and the oligomer and the polymer were separated. The obtained polymer was dried at 60° C. overnight under reduced pressure to obtain a first vinyl group-containing linear organopolysiloxane (A1-1) (Mn=277,734, Mw=573,906, IV value (dl/g) 0.89).

[Chem. 10]

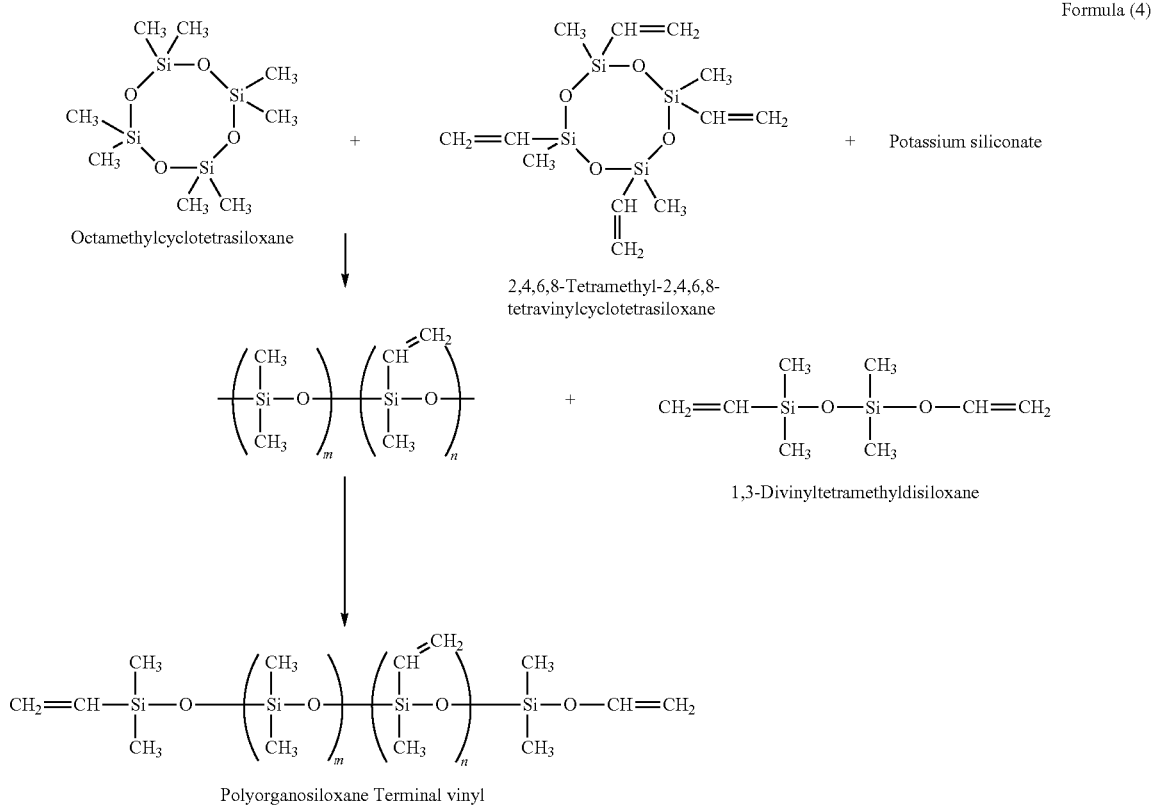

Formula (4)

Synthesis of Second Vinyl Group-Containing Linear Organopolysiloxane (A1-2)

In the same manner as described above the except that 2,4,6,8-tetramethyl-2,4,6,8-tetravinylcyclotetrasiloxane was used in the amount of 0.86 g (2.5 mmol) in the synthesis of (A1-1), a second vinyl group-containing organopolysiloxane (A1-2) was synthesized.-

2. Preparation of Silicone Rubber-Based Curable Composition

Example 11

First, 100 parts by weight of a vinyl group-containing linear organopolysiloxane (A1) [(A1-1):(A1-2)=80 parts by weight:20 parts by weight] was kneaded with 9.5 parts by weight of hexamethyldisilazane (D-1), 1.0 part by weight of divinyltetramethyldisilazane (D-2), and 5.25 parts by weight of water (F) in advance, and then 50 parts by weight of silica particles (C-1) was added thereto, followed by kneading them, to obtain a kneaded product (silicone rubber compound).

Further, the kneading after the addition of the silica particles (C-1) was carried out for a coupling reaction by conducting a first step of kneading for 1 hour under the conditions of 60 to 90° C. under a nitrogen atmosphere and a second step of kneading for 2 hours under the condition of 160 to 180° C. so as to remove the by-product (ammonia) under reduced pressure.

In addition, the obtained kneaded product was cooled to room temperature.

Then, to this kneaded product were added 0.49 parts by weight of the linear organohydrogen polysiloxane (B1), 0.16 parts by weight of the branched organohydrogen polysiloxane (B2), and 0.05 parts by weight of the platinum compound (E), followed by kneading them by a roll, to obtain a silicone rubber-based curable composition.

Example 12

In the same manner as in Example 11 except that the linear organohydrogen polysiloxane (B1) and the branched organohydrogen polysiloxane (B2) were added in the amounts of 0.42 parts by weight and 0.14 parts by weight, respectively, a silicone rubber-based curable material was prepared.

Example 13

First, 100 parts by weight of a vinyl group-containing linear organopolysiloxane (A1) [(A1-1):(A1-2)=80 parts by weight:20 parts by weight] was kneaded with 10.0 parts by weight of hexamethyldisilazane (D-1), 0.5 parts by weight of divinyltetramethyldisilazane (D)-2), and 5.25 parts by weight of water (F) in advance, and then 50 parts by weight of silica particles (C-1) was added thereto, followed by kneading them, to obtain a kneaded product (silicone rubber compound).

In addition, the obtained kneaded product was cooled to room temperature.

Then, to this kneaded product were added 0.35 parts by weight of the linear organohydrogen polysiloxane (B1), 0.12 parts by weight of the branched organohydrogen polysiloxane (B2), and 0.05 parts by weight of the platinum compound (E), followed by kneading them by a roll, to obtain a silicone rubber-based curable composition.

Reference Example 1

In the same manner as in Example 11 except that the linear organohydrogen polysiloxane (B1) was added in the amount of 0.59 parts by weight as the organopolysiloxane (B), a silicone rubber-based curable composition was prepared.

Reference Example 2

In the same manner as in Example 13 except that the linear organohydrogen polysiloxane (B1) was added in the amount of 0.49 parts by weight as the organopolysiloxane (B), a silicone rubber-based curable composition was prepared.

3. Evaluation

The obtained silicone rubber-based curable compositions of Examples 11 to 13 and Reference Examples 1 and 2 were evaluated by the following method.

3-1. Tensile Strength and Tear Strength

The silicone rubber-based curable compositions of Examples 11 to 13 and Reference Examples 1 and 2 were pressed at 170° C. and 10 MPa for 10 minutes, and molded into a 1 mm sheet shape, while carrying out a first curing. Subsequently, the composition was heated at 200° C. for 4 hours and subjected to a second curing.

Further, using the obtained silicone rubber in the sheet shape, a dumbbell-shaped #3 type test piece was prepared in accordance with JIS K6251 (2004), a crescent type test piece was prepared in accordance with JIS K6252 (2001), the tensile strength of the dumbbell-shaped #3 type test piece was measured in accordance with JIS K6251 (2004), and the tear strength of the crescent type test piece was measured in accordance with JIS K6252 (2001).

However, the thickness of the test piece used for the measurement of the tensile strength and the tear strength was set to 1 mm.

3-2. Evaluation of Hardness

For the silicone rubber-based curable compositions of Examples 11 to 13 and Reference Examples 1 and 2, silicone rubber in the sheet shape was prepared in the same manner as for the tensile strength and the tear strength, and the Type A durometer hardness was measured in accordance with JIS K6253 (1997). The thickness of the test piece was set to 6 mm or more by laminating 1 mm sheets.

3-3. Evaluation of Compression Permanent Strain

The silicone rubber-based curable compositions of Examples 11 to 13 and Reference Examples 1 and 2 were pressed at 170° C. and 10 MPa for 10 minutes, and molded into a sheet shape having a desired thickness of 4.5 mm, while carrying out a first curing. Subsequently, the composition was heated at 200° C. for 4 hours and subjected to a second curing.

Further, a test piece forming a cylindrical shape was prepared by punching the obtained silicone rubber in the sheet shape in the thickness direction to a size of a diameter of 29 mm.

Subsequently, in a state in which a spacer having a thickness of 3.5 mm was interposed between two substrates, the obtained test piece was clamped by these substrates. That is, a test piece having a thickness of about 4.5 mm was compressed to a thickness of 3.5 mm.

Incidentally, prior to compressing the test piece, the thickness (original thickness; mm) of each the test piece was measured. Further, the time taken for the clamping of the test piece to the substrate was set to 24 hours and the temperature of the atmosphere at the time of the clamping was set to 175° C.

Then, by measuring the thickness (mm) after 30 minutes from the removal of the compressive force, the compression permanent strain (CS) after a predetermined time was calculated using the following formula (a).

$$CS = \{(t0-t1)/(t0-t2)\} \times 100(\%) \qquad (a)$$

(in the formula (a), CS represents a compression permanent strain (%), t0 represents the original thickness of a test piece, t1 represents the thickness of the test piece after the removal of the compression force, and t2 represents the thickness of a spacer)

The evaluation results in the silicone rubber-based curable compositions of Examples 11 to 13 and Reference Examples 1 and 2 obtained as above are shown in Table 2 below.

called waist), low kink resistance, and generation of obstruction. To the contrary, by promoting the silicone rubber having a high hardness, a high modulus, and a high restorability (high rubber elasticity), a catheter formed from the silicone rubber solves the above-described problem.

From the description above, the present invention is extremely useful industrially.

TABLE 2

| | Vinyl group-containing linear polyorgano-siloxane (A1) | | Organohydrogen siloxane (B) | | Silica particles (C) | | Silane coupling agent (D) | | | | | |
|---|---|---|---|---|---|---|---|---|---|---|---|---|
| | Low vinyl rubber (A1-1) (parts) | High vinyl rubber (A1-2) (parts) | Linear (B1) (parts) | Branched (B2) (parts) | Specific surface area (m2/g) | Filling amount (parts) | Hexamethyl-disilazane (D-1) (parts) | Tetramethyl-divinyldisilazane (D-2) (parts) | Tear strength N/mm | Hardness TYPE A | Tensile strength MPa | Compression permanent strain % |
| Example 11 | 80.0 | 20.0 | 0.49 | 0.16 | 300 | 50 | 9.5 | 1.0 | 59.0 | 59 | 9.6 | 30.5 |
| Example 12 | 80.0 | 20.0 | 0.42 | 0.14 | 300 | 50 | 9.5 | 1.0 | 49.2 | 59 | 8.9 | 31.7 |
| Example 13 | 80.0 | 20.0 | 0.35 | 0.12 | 300 | 50 | 10.0 | 0.5 | 51.2 | 52 | 9.0 | 24.3 |
| Reference Example 1 | 80.0 | 20.0 | 0.59 | 0.00 | 300 | 50 | 9.5 | 1.0 | 51.2 | 55 | 7.9 | 45.0 |
| Reference Example 2 | 80.0 | 20.0 | 0.49 | 0.00 | 300 | 50 | 10.0 | 0.5 | 54.6 | 51 | 8.5 | 35.4 |

As shown in Table 2, as compared with Reference Example 1 in Examples 11 and 12, and similarly, as compared with Reference Example 2 in Example 13, a result was obtained that a silicone rubber having excellent strength and a low compression permanent strain while having an approximately equivalent hardness could be obtained by using a configuration including both of the linear organohydrogen polysiloxane (B1) and the branched organohydrogen polysiloxane (B2) as the organohydrogen polysiloxane (B). This is presumed to be due to the fact that the crosslink density becomes higher with the use of such an organohydrogen polysiloxane (B).

INDUSTRIAL APPLICABILITY

The silicone rubber obtained by curing the silicone rubber-based curable composition of the present invention, that is, the silicone rubber produced by the method for producing a silicone rubber of the present invention has excellent tensile strength and tear strength as well as a low compression permanent strain. Accordingly, the molded article and the tube for medical use formed from the molded article, each formed using the obtained silicone rubber have high mechanical strength such as tensile strength and tear strength, and a low compression permanent strain.

Furthermore, a high hardness, a high modulus, and a high restorability (high rubber elasticity) of the silicone rubber thus formed are promoted by using a silane coupling agent having a vinyl group as a silane coupling agent included in the silicone rubber-based curable composition.

Here, the silicone rubber as a material of a catheter for medical use is required to have a certain degree of hardness. For example, a catheter formed from a material having a low hardness easily causes problems, for example, generation of deformation by insertion resistance upon insertion into a target site (for example, thoracic cavity) (there is no so-

The invention claimed is:

1. A silicone rubber-based curable composition comprising:
   a vinyl group-containing organopolysiloxane (A);
   an organohydrogen polysiloxane (B), wherein the organohydrogen polysiloxane (B) is a linear organohydrogen polysiloxane (B1), and the linear organohydrogen polysiloxane (B1) does not contain a vinyl group;
   silica particles (C);
   a silane coupling agent (D); and
   a platinum or a platinum compound (E),
   wherein the vinyl group-containing organopolysiloxane (A) is a vinyl group-containing linear organopolysiloxane (A1),
   wherein the vinyl group-containing linear organopolysiloxane (A1) contains a first vinyl group-containing linear organopolysiloxane (A1-1) and a second vinyl group-containing linear organopolysiloxane (A1-2), the first vinyl group-containing linear organopolysiloxane (A1-1) having a content of the vinyl groups different from that of the second vinyl group-containing linear organopolysiloxane (A1-2),
   the silane coupling agent (D) has a hydrolyzable group, and the hydrolyzable group is a silazane group,
   the silica particles (C) are contained in a proportion of 35 parts by weight to 75 parts by weight, with respect to 100 parts by weight of the total amount of the vinyl group-containing organopolysiloxane (A) and the organohydrogen polysiloxane (B), and
   the silane coupling agent (D) is contained in a proportion of 5 parts by weight to 100 parts by weight, with respect to 100 parts by weight of the silica particles (C).

2. The silicone rubber-based curable composition according to claim 1, further comprising water (F).

3. The silicone rubber-based curable composition as described in claim 1, wherein the silane coupling agent (D) is at least one selected from the group consisting of hexamethyldisilazane and divinyltetramethyldisilazane.

4. The silicone rubber-based curable composition according to claim 3, wherein the vinyl group-containing linear organopolysiloxane (A1) is represented by the following formula (1):

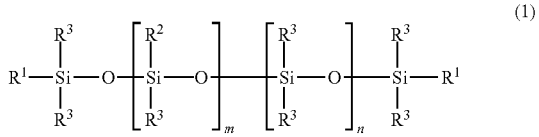

(1)

in the formula (1), m is an integer of 1 to 1000, n is an integer of 3000 to 10000, $R^1$ is a substituted or unsubstituted alkyl group, alkenyl group, or aryl group having 1 to 10 carbon atoms, or a hydrocarbon group formed by the combination of these groups, $R^2$ is a substituted or unsubstituted alkyl group, alkenyl group, or aryl group having 1 to 10 carbon atoms, or a hydrocarbon group formed by the combination of these groups, and $R^3$ is a substituted or unsubstituted alkyl group or aryl group having 1 to 8 carbon atoms, or a hydrocarbon group formed by the combination of these groups.

5. The silicone rubber-based curable composition according to claim 1, wherein the content of the vinyl groups of the first vinyl group-containing linear organopolysiloxane (A1-1) is from 0.05% by mole to 0.2% by mole, and the content of the vinyl groups of the second vinyl group-containing linear organopolysiloxane (A1-2) is from 0.5% by mole to 12% by mole.

6. The silicone rubber-based curable composition according to claim 1, wherein the linear organohydrogen polysiloxane (B1) is represented by the following formula (2):

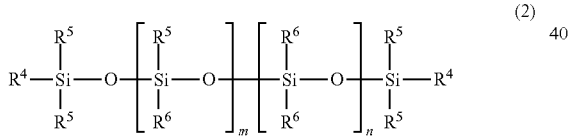

(2)

in the formula (2), m is an integer of 0 to 300 and n is an integer of (300-m). $R^4$ is a substituted or unsubstituted alkyl group, or aryl group having 1 to 10 carbon atoms, a hydrocarbon group formed by the combination of these groups, or a hydride group; $R^5$ is a substituted or unsubstituted alkyl group, or aryl group having 1 to 10 carbon atoms, a hydrocarbon group formed by the combination of these groups, or a hydride group; however, at least two or more out of plural $R^4$s and $R^5$s are hydride groups; $R^6$ is a substituted or unsubstituted alkyl group or aryl group having 1 to 8 carbon atoms, or a hydrocarbon group formed by the combination of these groups.

7. The silicone rubber-based curable composition according to claim 1, further comprising a branched organohydrogen polysiloxane having a branched structure (B2).

8. The silicone rubber-based curable composition according to claim 7, further comprising water (F).

9. The silicone rubber-based curable composition according to claim 7, wherein the vinyl group-containing linear organopolysiloxane (A1) is represented by the following formula (1):

[化3]

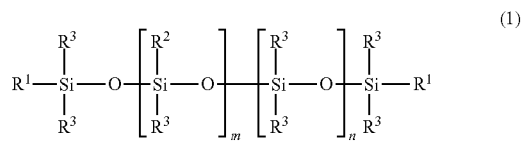

(1)

in the formula (1), m is an integer of 1 to 1000, n is an integer of 3000 to 10000, R1 is a substituted or unsubstituted alkyl group, alkenyl group, or aryl group having 1 to 10 carbon atoms, or a hydrocarbon group formed by the combination of these groups, R2 is a substituted or unsubstituted alkyl group, alkenyl group, or aryl group having 1 to 10 carbon atoms, or a hydrocarbon group formed by the combination of these groups, R3 is a substituted or unsubstituted alkyl group or aryl group having 1 to 8 carbon atoms, or a hydrocarbon group formed by the combination of these groups.

10. The silicone rubber-based curable composition according to claim 7, wherein the linear organohydrogen polysiloxane (B1) is represented by the following formula (2):

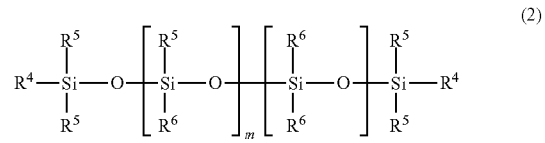

(2)

in the formula (2), m is an integer of 0 to 300 and n is an integer of (300-m). R4 is a substituted or unsubstituted alkyl group, or aryl group having 1 to 10 carbon atoms, a hydrocarbon group formed by the combination of these groups, or a hydride group; R5 is a substituted or unsubstituted alkyl group, or aryl group having 1 to 10 carbon atoms, a hydrocarbon group formed by the combination of these groups, or a hydride group; however, at least two or more out of plural R4s and R5s are hydride groups; R6 is a substituted or unsubstituted alkyl group or aryl group having 1 to 8 carbon atoms, or a hydrocarbon group formed by the combination of these groups.

11. A silicone rubber-based curable composition comprising:
   a vinyl group-containing organopolysiloxane (A);
   an organohydrogen polysiloxane (B);
   silica particles (C);
   a silane coupling agent (D); and
   a platinum or a platinum compound (E),
   wherein the vinyl group-containing organopolysiloxane (A) is a vinyl group-containing organopolysiloxane (A1),
   wherein the organohydrogen polysiloxane (B) comprises both of a linear organohydrogen polysiloxane having a linear structure (B1) and a branched organohydrogen polysiloxane having a branched structure (B2),
   wherein the branched organohydrogen polysiloxane (B2) is represented by the following average composition formula (c):
   average composition formula (c): $(H_a(R^7)_{3-a}SiO_{1/2})_m(SiO_{4/2})_n$ in the formula (c), $R^7$ is a monovalent organic group, a is an integer in the range of 1 to 3, m is the number of $H_a(R^7)_{3-a}SiO_{1/2}$ units, and n is the number of $SiO_{4/2}$ units, wherein the silica particles (C) are contained in a proportion of 35 parts by weight to 75 parts by weight, with respect to 100 parts by weight of the total amount of the vinyl group-containing organopolysiloxane (A) and the organohydrogen polysiloxane (B), and wherein the silane coupling agent (D) is contained in a proportion of 5 parts by weight to 100 parts by weight, with respect to 100 parts by weight of the silica particles (C).

12. A method for producing a silicone rubber, comprising:
a step of obtaining a kneaded product containing a vinyl group-containing organopolysiloxane (A), silica particles (C), and a silane coupling agent (D);
a step of obtaining a silicone rubber-based curable composition by kneading the kneaded product with an organohydrogen polysiloxane (B) and a platinum or a platinum compound (E); and
a step of forming a silicone rubber by curing the silicone rubber-based curable composition,
wherein the organohydrogen polysiloxane (B) is a linear organohydrogen polysiloxane (B1), and the linear organohydrogen polysiloxane (B1) does not contain a vinyl group
wherein the vinyl group-containing organopolysiloxane (A) is a vinyl group-containing linear organopolysiloxane (A1), and the vinyl group-containing linear organopolysiloxane (A1) contains a first vinyl group-containing linear organopolysiloxane (A1-1) and a second vinyl group-containing linear organopolysiloxane (A1-2), the first vinyl group-containing linear organopolysiloxane (A1-1) having a content of the vinyl groups different from that of the second vinyl group-containing linear organopolysiloxane (A1-2), and
wherein the silane coupling agent (D) has a hydrolyzable group, and the hydrolyzable group is a silazane group
wherein the silica particles (C) are contained in a proportion of 35 parts by weight to 75 parts by weight, with respect to 100 parts by weight of the total amount of the vinyl group-containing organopolysiloxane (A) and the organohydrogen polysiloxane (B), and the silane coupling agent (D) is contained in a proportion of 5 parts by weight to 100 parts by weight, with respect to 100 parts by weight of the silica particles (C).

13. The method for producing a silicone rubber according to claim 12, wherein the silicone rubber-based curable composition is obtained by further adding a branched organohydrogen polysiloxane (B2).

14. The silicone rubber-based curable composition according to claim 7, wherein the branched organohydrogen polysiloxane (B2) does not contain a vinyl group.

15. The method for producing a silicone rubber according to claim 12, wherein the silane coupling agent (D) is selected from the group consisting of hexamethyldisilazane, and divinyltetramethyldisilazane.

* * * * *